United States Patent [19]

Goldberg

[11] 4,034,744

[45] July 12, 1977

[54] ULTRASONIC SCANNING SYSTEM WITH VIDEO RECORDER

[75] Inventor: Paul R. Goldberg, Palo Alto, Calif.

[73] Assignee: Smith Kline Instruments, Inc., Sunnyvale, Calif.

[21] Appl. No.: 631,623

[22] Filed: Nov. 13, 1975

[51] Int. Cl.² .................................... A61B 10/00
[52] U.S. Cl. .......................... 128/2 V; 73/67.8 S; 128/2.05 Z
[58] Field of Search ............. 128/2 V, 2 R, 2.05 Z; 73/67.8 S

[56] References Cited

U.S. PATENT DOCUMENTS

| | | | |
|---|---|---|---|
| 3,547,101 | 12/1970 | Rosauer | 128/2 V |
| 3,690,311 | 9/1972 | Schorum et al. | 128/2 V |
| 3,778,756 | 12/1973 | Houston et al. | 128/2.05 Z X |
| 3,779,234 | 12/1973 | Eggleton et al. | 128/2 V |
| 3,817,089 | 6/1974 | Eggleton et al. | 73/67.8 S |
| 3,828,609 | 8/1974 | Furon et al. | 73/67.8 S |

*Primary Examiner*—Kyle L. Howell

[57] ABSTRACT

An ultrasonic scanning system for observing the internal organs of the body including at least one ultrasonic transducer for sequentially scanning a region of the body and pulsing means for periodically pulsing said transducer as it begins a scan. Video recording means records a composite signal including scanning, pulse rate and echo information for reproduction. Display means are included for directly displaying the information or for displaying the play-back from the video recorder. The display is interlaced, providing minimum jitter and maximum resolution.

12 Claims, 8 Drawing Figures

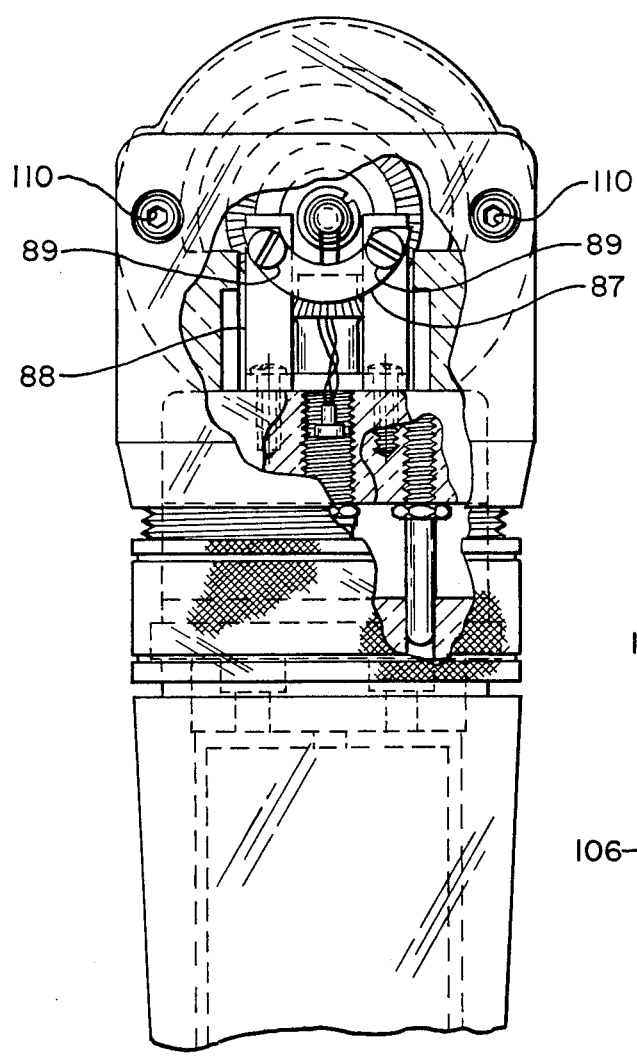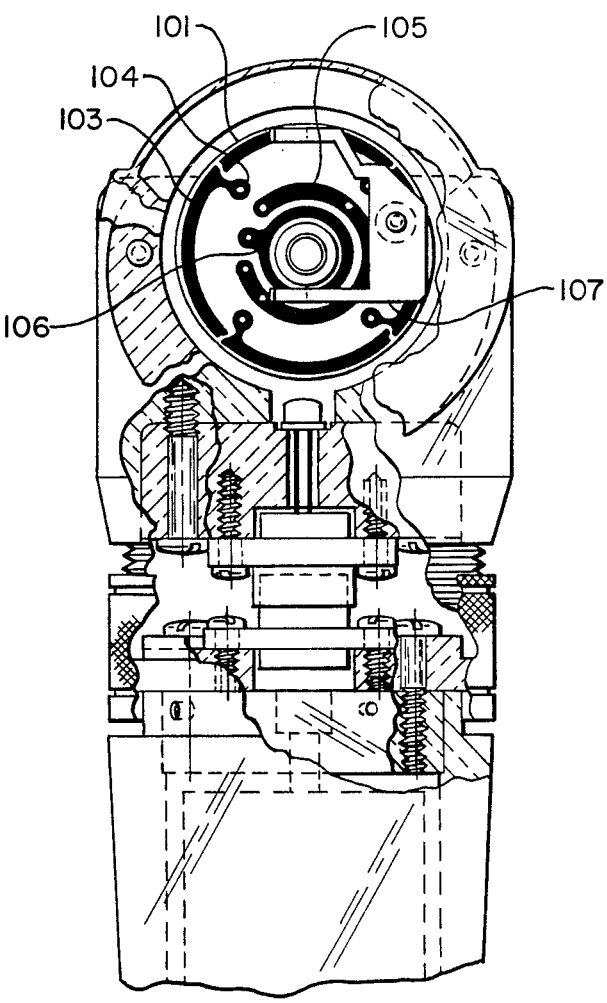
FIG.-7
FIG.-8

ULTRASONIC SCANNING SYSTEM WITH VIDEO RECORDER

BACKGROUND OF THE INVENTION

This invention relates generally to ultrasonic scanning systems for use in observing organs in the body and more particularly to an ultrasonic sector scanning system.

In recent years ultrasonic scanning of regions of the human body has found wide applications. Among the advantages of such scanning systems is that the energy required is low, greatly reducing the possibility of injury to the patient; there are no side effects of radiation; and the body is not invaded.

The ultrasound is transmitted in a beam including brief pulses each followed by a relatively long interval where no transmission occurs. During this interval the pulse energy is transmitted through the body. Whenever a pulse of energy strikes a boundary between two substances having different acoustic impedances, a portion of the energy is reflected, some of it returning as an echo to the source. The remaining portion of the original energy is available to produce additional echoes from deeper interfaces. The crystal which serves as the transducer converting electrical energy into sound pulses receives the echoes and generates an electrical signal. This signal is amplified, displayed as a static or dynamic pattern on a cathode ray tube. The relative positions of the interfaces are shown on the display.

A particular type of scanner used is a sector scanner since it has the ability to display a cross-sectional area of the human body. A sector scanner generally comprises an ultrasonic transducer (a piezoelectric element) which is mounted and motor driven through a suitable mechanical arrangement. The drive arrangement moves the transducer which is generally in the form of a flat circular object back and forth in an arc scanning motion. During this process, the transducer is pulsed with high voltage spikes at pulsed repetition rates in the order of 3000 Hz. These spikes cause the piezoelectric element to mechanically ring, thereby emitting high frequency sound waves. These ultrasonic waves impinge upon the structure within the body and, when difference of acoustic impedance exists, are partially reflected back to the transducer element. At this point, the transducer element acts like a receiver and converts these mechanical vibrations to electrical energy. This energy is amplified and processed such that it can be displayed on a cathode ray tube.

The mechanical driving arrangement not only drives the probe but also provides an electrical output analogous to transducer position by the use of position sensing means such as a potentiometer which translates position information into electrical energy. The electrical signal is processed and utilized to create horizontal and vertical signals which, along with the returning ultrasonic impulses, are used to create an X-Y display on the cathode ray tube. The resultant image is a representation of the internal organs of the body.

In order for the information displayed on the cathode ray tube monitor to be most effective in use, it is necessary to record these images so that they can later be viewed and compared. The methods presently employed take the form of a movie camera photographing the monitor display or a television camera focused on the monitor connected to a video tape recorder. Electrostatic and similar printers have also been used.

Another prior art system which allows real time examination of internal organs of the body such as the heart employs a catheter which has a rotating tip which carries a plurality of transducers. The transducers are selectively connected to a pulser to transmit ultrasonic pulses into the body and to receive echoes therefrom. The echo pulses are processed and applied to a cathode ray tube whereby they provide sequential representations of the area at a rate which is dependent upon the speed of rotation of the transducers and with a resolution which is dependent upon the pulse rate. Field rates are selected so that the display can be photographed with a movie camera, for example, 24 frames per second. The system briefly described above is the subject of U.S. Pat. No. 3,779,234.

In all the prior methods there is no system approach. Each device, display and recorder, operate in their normal mode. There is no attempt to combine the characteristics and advantages of each to obtain a better result and reduce the overall cost of the system.

SUMMARY AND OBJECTS OF THE INVENTION

It is a general object of the present invention to provide an improved ultrasonic sector scanning system.

It is another object of the present invention to provide an ultrasonic sector scanning system in which the scanning information is displayed and directly recorded in a video recorder.

It is another object of the present invention to provide a sector scanning system in which the display is interlaced to provide a flicker-free high resolution display.

These and other objects of the invention are achieved by a system which includes at least one ultrasonic transducer adapted to receive electrical pulses and transmit an ultrasonic beam into the body and which receives reflected ultrasonic energy and generates an electrical signal. Means are provided for moving the transducer so that it periodically scans a predetermined sector in a predetermined time. Pulses are applied at a predetermined rate whereby the time and rate determines the number of lines scanned in each field. A video recording means is connected to the scanning system and serves to record a composite signal of the scan field including information respecting the beginning of each scan line and scan field and the transducer output whereby when the recording is reproduced, processed and applied to display means, it provides a display which corresponds exactly to the original display. The system also includes means for providing a display as the information is recorded.

BRIEF DESCRIPTION OF THE DRAWING

FIG. 7 is a view of one side of the head portion partly broken away to show the interior components.

FIG. 8 is a view of the opposite side of the head partly broken away to show the interior components.

DESCRIPTION OF PREFERRED EMBODIMENTS

Figure 1:
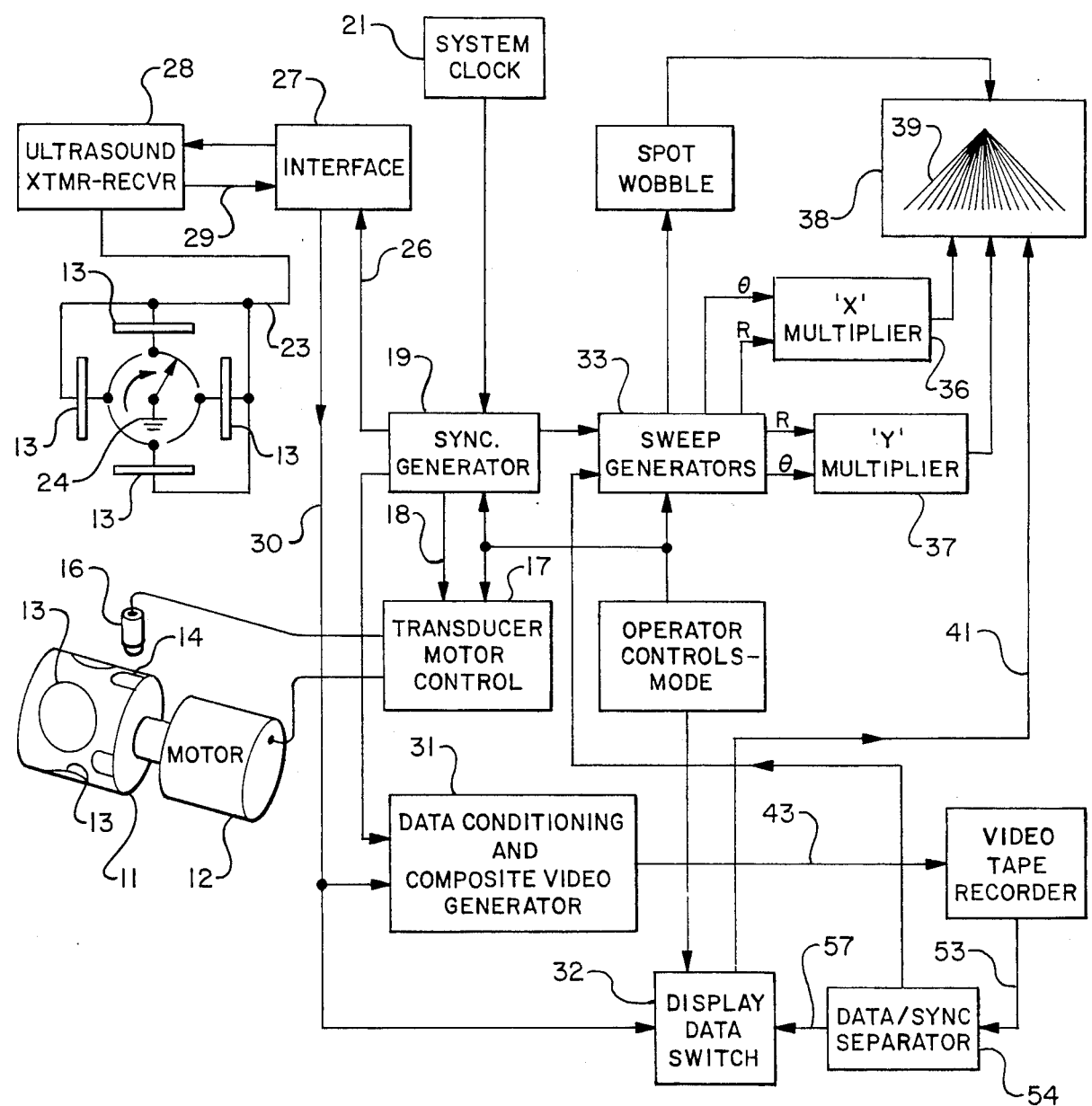
FIG. 1 is a block diagram of a system in accordance with the present invention.

The system described includes a rotor 11 driven by a motor 12. The rotor 11 carries a plurality of ultrasonic transducers 13 spaced about the periphery of the rotor. The rotating member 11 also carries a plurality of spaced reflecting surfaces 14 which are viewed by a phototransducer 16 which provides an output pulse as each reflective surface 14 passes the phototransducer. The output of the phototransducer 16 is applied to motor control 17 to which is also applied a reference frequency along the line 18 from sync generator 19 which serves to synchronize the operation of the overall system as will be presently described. Input to the sync generator is from a clock system 21 which may include a crystal together with appropriate dividers to provide a control frequency to the sync generator 19. The output on the line 18 may, for example, be a 60 Hertz output which is applied to the motor control. The output pulses from the phototransducer 16 are employed in a servo system to servo control operation of the motor 12 and to control the position of the rotor 11 whereby the position of the transducer is accurately determined as the rotor rotates. Ultrasonic pulses are applied sequentially to the individual transducers at a high rate so that they scan a plurality of lines in a fan or sector as the member rotates. This is schematically shown in the Figure where the transducers 13 are shown with one side connected to a common input line 23 with the other side adapted to be connected to ground 24 as the rotor rotates. Consequently, only one of the transducers is connected during 90° of rotation. The arrangement is such that as one transducer scans a 90° sector, the next transducer begins to scan the same 90° sector in sequence.

Figure 2:
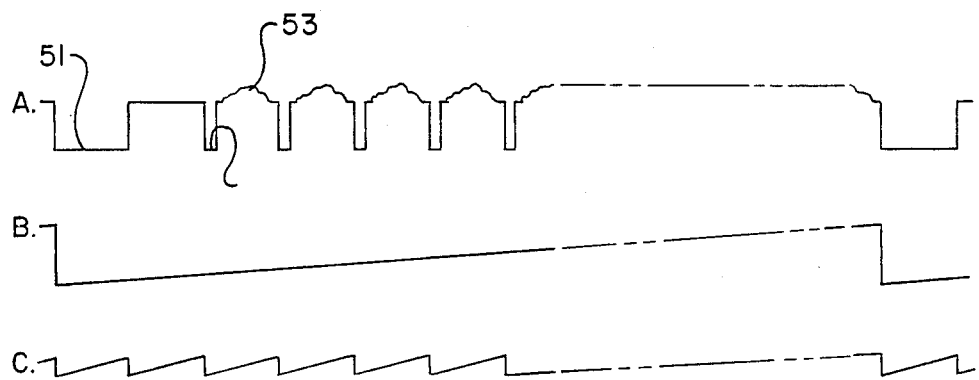
FIG. 2 is a timing diagram showing the waveforms at various portions of the system of FIG. 1.
Figure 3:
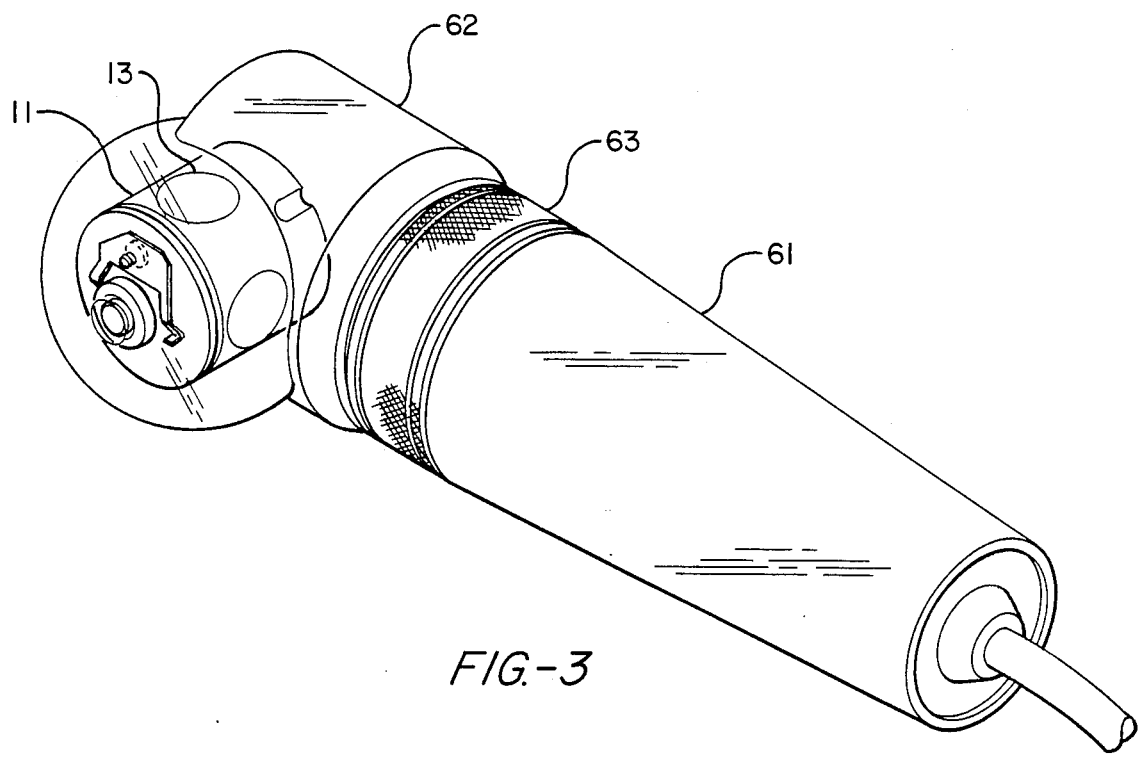
FIG. 3 is a perspective view of a scanning head suitable for use in the system of the present invention.
Figures 5, 6:
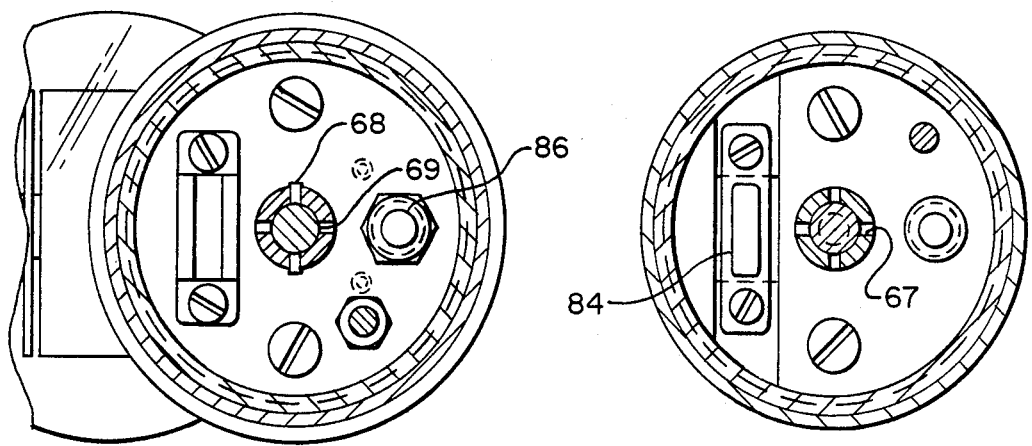
FIGS. 5 and 6 are sectional views taken along the lines 5—5 and 6—6 of FIG. 4 respectively.

The sync generator 19 applies trigger pulses along the line 26 to an interface 27 which drives a suitable transmitter and receiver 28. For example, the transmitter-receiver may be an Ekoline 20A/B which serves to receive trigger pulses and transmit ultrasonic pulses for application to the transducer. The transducer receives the echoes from the interfaces and the receiver processes the same and provides ultrasound data along the line 29 to the interface 27. The ultrasound data appears on the line 30 and is applied to a data conditioning and composite video generator 31 and to a display data switch 32. At the beginning of each trigger pulse, the sync generator 19 applies a sync pulse to the sweep generator 33 which serves to form a plurality of sawtooth voltage waves such as shown in FIG. 2C. The sawtooth voltage waves provide the so-called "R" sweep voltage which is modified as will be presently described. In addition, the sync generator also serves to generate a trigger pulse responsive to the output from the transducer 16 to thereby indicate the beginning of a sweep. This trigger pulse serves to form a sawtooth voltage such as shown in FIG. 2B which provides the $\theta$ sweep voltage which is also modified. The R and $\theta$ sweep voltages are then applied to X and Y multipliers 36 and 37 which provide outputs equal to $X = R \sin \theta$ and $Y = R \cos \theta$, respectively. This causes the sweep of the oscilloscope to be such as shown at 38 comprising a 90° scan with a plurality of scan lines 39 each beginning with the application of a pulse to the transducer and each field or scan representing 90° rotation of the transducer. The number of lines is, therefore, directly dependent upon the frequency of the ultrasonic pulses which are applied to the transducers. The ultrasound data on the line 30 is applied through the display switch to the monitor along the line 41 and serves to modulate the intensity of the beam whereby the scan will be modulated in accordance with the ultrasound data which is received as a result of reflections from the interfaces. The speed of rotation of the rotor 11 determines the number of fields or displays which are available per second while the number of pulses applied determines the number of lines. It is apparent, however, that the pulse rate is limited by the depth which the scan must reach since there must be enough time between pulses to receive echoes from the deepest portion observed.

In accordance with the present invention, the sync signals from the sync generator 19 corresponding both to the R and $\theta$ sync signals applied to the sweep generators are also applied to a data conditioner 31. The data conditioner also receives the ultrasound data. The unit processes the data in a manner similar to a television composite signal generator. It provides a composite video signal on the line 43. The signal is illustrated at Figure 2A and includes vertical sync pulses 51, horizontal sync pulses 52 and the ultrasound data 53 for each scan line.

The video recorder may be any conventional video recorder such as a helical scan recorder which serves to record video signal. The rotation of the recording heads and the motion of the tape is synchronized with the timing system of the ultrasonic scanning system whereby to provide the recording of sequential fields of information.

During playback, the video recorder composite signal is applied along the line 53 to a data sync separator 54 which separates out the R and $\theta$ sync pulses and applies them to the sweep generator 33 which provides the appropriate sweep signals through the multipliers 36 and 37 for driving the deflection circuits of the cathode ray tube. The separated ultrasound data on the line 57 is applied to the display switch and directly to the video display in the same manner as the original ultrasound pulses to modulate the intensity. Thus, the playback display is identical to the original display.

In accordance with another feature of the present invention, the rate of rotation and the pulse rate are so selected that the scan lines are interlaced, that is, the scan lines for each sequential field are interlaced with the scan line of the previous field thereby giving a higher resolution without flicker.

More specifically, most video tape recorders commercially available are based on a helical scanning principle. The video recording tape is wrapped around a drum in which one or more record/playback heads are rotating. Each head protrudes through a slot which traverses the outer diameter of the drum. The tape is wrapped almost parallel to the plane of the moving head so that the head moves at an angle with respect to the longitudinal axis of the tape, thus generating a helical scanning pattern. Two television fields are recorded on the tape every one-thirtieth of a second. These fields by themselves do not represent the entire television picture. These two fields are required to create a television frame. The two fields are scanned onto a cathode ray tube screen in an interlaced pattern to provide the frame. That is, the first set of horizontal scan lines corresponding to one field is drawn on the phosphor screen, after which the second set corresponding to the other field is placed in the space between the first set of lines. This 2:1 interlacing technique provides the viewer with a high resolution, twice the resolution of either field separately.

If the sector scanning probe just described is built with four rotating transducer elements and the rotation is held in synchronism with the rotating heads of the video recorder, the ultrasonic signals produced will be recorded in the same field/frame format as would a television image. Assuming that the cylindrical transducer head makes a complete rotation in one-thirtieth of a second in 1:1 synchronism with the video tape recorder head, four fields per revolution are created if a four element head is chosen. Each field would contain a number of lines which would be determined by the pulse repetition rate at which the elements are driven and the length of time each transducer is actively being pulsed. In the above case, is a pulse repetition rate of 3000 Hz is chosen, there would be 25 lines per field.

In a practical system, a resolution of 25 lines per field over a 90° sector would be unacceptable even if there were 4:1 interlace. The system is, therefore, modified to increase the number of lines visualized on the display. This can be done by taking advantage of a slower rotary rate for the rotating head to provide more lines in each 90° segment (field) and interlacing a number of successive fields to form a flicker-free frame.

A suitable system would be for a transducer element rotating at 900 rpm pulsed at 3000 Hz and utilizing a 4:1 interlace. This would give 50 lines per field and 200 lines per frame. The display would be a 90° segment with an apparent 200 line resolution. Preferably, the interlace would be lines 1, 3, 2, 4. This would provide minimum flicker since the maximum time difference between any two adjacent lines would be only two fields.

For the interlace system to work with no inconsistencies in the final display, the number of lines per field and the interlace ratio must be precisely controlled from frame to frame. Therefore, the pulse repetition rate of the ultrasonoscope driving the rotating section transducer is synchronized with the rotating transducer head which is achieved by the sync generator in the present invention.

As earlier discussed, the mechanical driving arrangement of the prior art sector scanner provides an electrical output analogous to transducer position by use of a position sensing means. This electrical output is ultimately used to create the X-Y display on the cathode ray tube. The rotating sector transducer also provides a position signal. This signal is recorded on the video tape recorder in the present method and provides the field synchronizing pulse.

In order to play back the recorded sector scanning image, the position of the transducer element in each instant of time must be available to the X-Y display processing circuitry simultaneously with the appropriate ultrasonic information. This is provided by the line pulses recorded for each scan line. Upon reproduction from the video tape recorder, the timing information is recovered to drive the sweep generators. In order to provide an appropriate interlace, the number of lines per field are chosen to include a fractional portion, that is, if there is to be a 4:1 interlace, the lines per field would be 49.25 to provide the suitable interlace.

Figure 4:
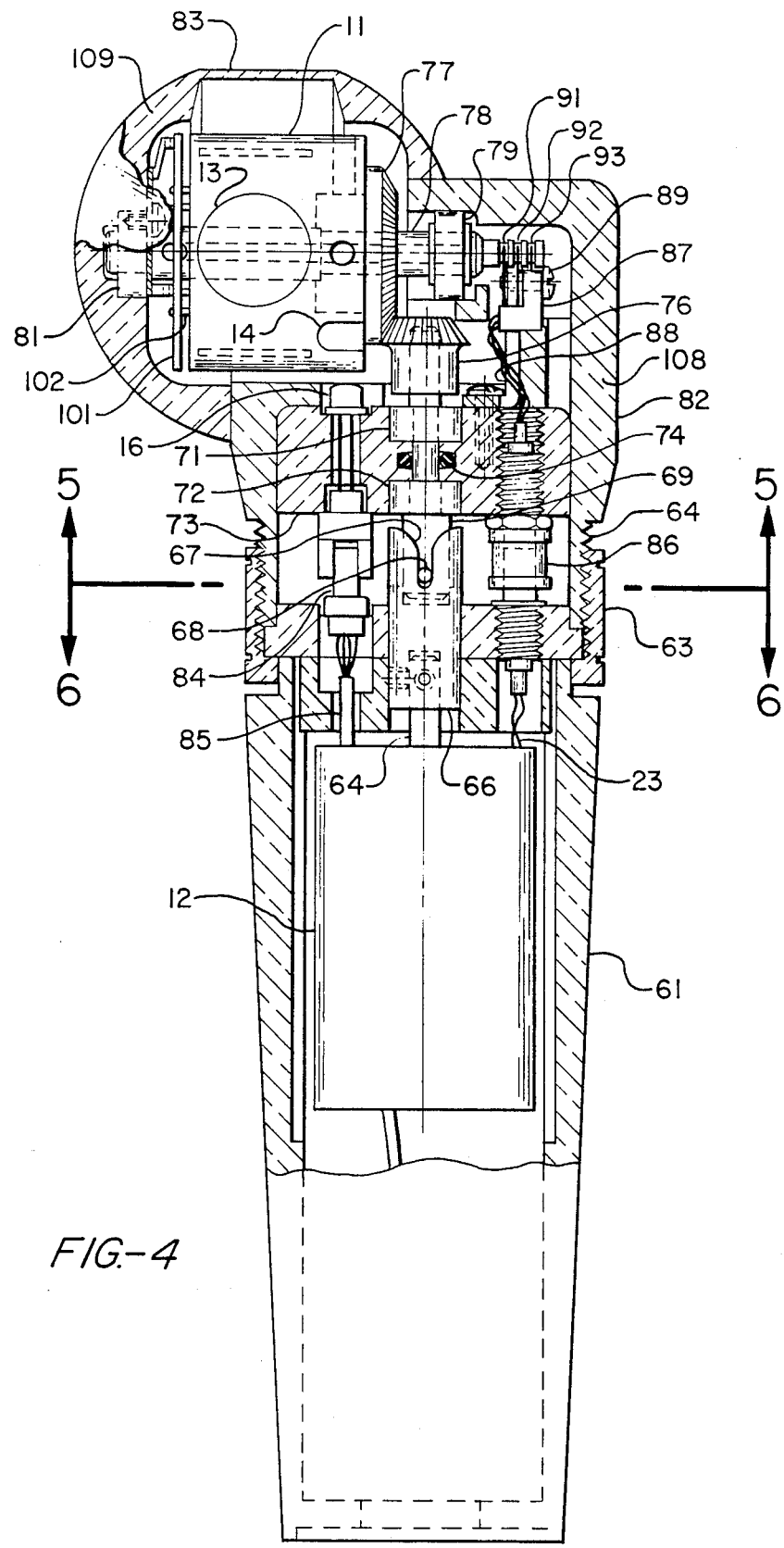
FIG. 4 is a sectional view of the scanning head partly broken away to show the interior components.

A suitable rotating head assembly and probe for use in connection with the present invention is shown in FIGS. 3 through 8. The rotating head assembly and probe form the subject matter of copending application Ser. No. 631,456 filed Nov. 13, 1975. The probe includes handle 61 which is detachably secured to a scanning head 62 by means of a ring 63 which engages threads 64 formed on the head 62 (FIG. 4). The attachment of the head 62 to the handle 61 provides a mechanical connection to the driving motor and an electrical connection to associated equipment as will be presently described.

The head 62 includes the rotor 11 with a plurality of transducers 13 which rotate in a plane parallel to the axis of the probe handle. Referring more particularly to FIG. 4, the handle 61 serves to house the motor 12 with the motor shaft 64 attached to coupler 66. The coupler has its forward end slotted with two crossing slots 67 as shown more particularly in FIG. 6. The slots 67 are adapted to engage pin 68 mounted on driven shaft 69. The driven shaft 69 is mounted for rotation by spaced bearings 71 and 72 mounted in the disc shaped mounting block 73. An O-ring seal 74 serves to seal the shaft and prevent leakage of ultrasound transmitting fluid which fills the head portion as will be presently described. Opinion gear 76 is mounted on the end of the shaft and engages bevel gear 77 mounted on the rotor shaft 78. Thus, rotation of the motor serves to rotate the rotor 11. The rotor 11 is supported for rotation by a shaft 78 which is mounted on spaced bearings 79 and 81. The complete assembly just described is housed within a shell or cover 82 which has a relatively thin portion 83 adjacent the probe face to thereby permit the transmission of ultrasonic energy. The complete interior of the housing is filled with a suitable fluid which provides continuity for the transmission of the ultrasonic energy from the transducers 13 to and through the window 83. The window 83 is adapted to be placed against the body to be examined. An interface is applied to the body for transmission of the ultrasound into the body with minimum losses at the interfaces. As previously described, the rotor includes a plurality of reflective surfaces 14. The phototransducer 16 cooperates with the surfaces and provides an output signal through a connector 84 to the cable 85 carried by the handle. The ultrasound pulses are applied to the wires 23 through a coaxial connector 86 to the brush block 87 suitably attached to the mounting brackets 88 by screws 89. The brushes 91, 92 and 93 ride within associated grooves formed on the extension of the shaft 78. Slip rings are carried in the grooves and are connected to leads which run coaxially within the hollow shaft 78 and exit at the opposite end of the rotor as will be presently described. The brush block and its mounting is more clearly shown in FIG. 7 and includes a pair of screws 89 attaching the brush block 87 to L-shaped support 88 which, in turn, are secured to the disc 73.

Referring to FIG. 8, the commutating system at the end of the rotor is more clearly shown. The system includes a printed circuit board 101 suitably attached to the rotor as, for example, by pins 102, FIG. 4. The commutating system includes four commutating segments 103, each having one end 104 connected to an associated transducer and extending approximately 90°. The ultrasonic energy is directed coaxially through the shaft and connected to the continuous commutating ring 106. A brush 107 serves to provide contact between the rings 106 and segments 103 whereby as the rotor is rotated, the ring 106 is sequentially connected to each of the segments 103 to sequentially connect one side of each of the transducers to the source of energy. The other side of each of the transducers is connected to a ring 105 which is, in turn, connected to ground to provide the other terminal for the transducers. The rotor housing 82 includes a first portion 108 which is threaded and adapted to be engaged by the ring 63 and a second substantially hemispherical portion 109 adapted to be attached thereto so that the rotor and associated parts can be placed within a fluid-tight housing. The hemispherical portion 109 is suitably secured to the portion 108 by means of screws 110 of FIG. 7. A suitable sealant is provided between the spherical portions and the intersecting surfaces of the portion 108. Thus, it is seen that there is provided a compact, movable probe which can be easily applied to the body for scanning particular section thereof. In the event that different transducer characteristics are required, the head portions can be removed and a new head inserted. For example, a head having three or two transducers may be employed in connection with the motor handle 61.

Although the system described above operates by synchronously recording on the recording medium the fields and lines scanned by the transducer with the motion of the recording head, it is possible to operate asynchronously. That is, the movement of the ultrasonic transducer need not by synchronous with the movement of the recording heads.

Thus, there has been described an ultrasonic scanning system which efficiently integrates a video recorder with an ultrasonic scanner to provide a high resolution flicker-free display of the information regarding interfaces in the body being scanned.

What is claimed is:

1. An ultrasonic scanning system including at least one ultrasonic transducer adapted to receive electrical pulses and transmit an ultrasonic beam and to receive ultrasonic energy and generate an electrical signal, means for causing said beam to periodically scan a predetermined sector in a predetermined time, means providing a signal at the beginning of each scan sector, means for applying pulses to the transducer at a predetermined rate to form a plurality of ultrasonic pulses which travel in scan lines, the period of said scan and rate of said pulses determining the number of scan lines scanned in each sector, a video recording means connected to said scanning system and serving to record a composite signal including said beginning of scan signal for each scan sector, the application of said pulses to form scan lines and the transducer output whereby when the recording is reproduced, processed and applied to control display means it forms a display of the scanned lines in said sector.

2. An ultrasonic scanning system as in claim 1 including means for processing the signal respecting the beginning of said scan sector, the application of said pulses and the transducer output and for directly applying the processed information to a display means during recording whereby said display means forms a display of the information which is being recorded.

3. An ultrasonic scanning system as in claim 1 wherein said ultrasonic transducer includes a plurality of transducers adapted to sequentially scan the sector with the scan line of each transducer beginning at a different angle whereby when the signal is reproduced and sequential sectors are applied to the display means the scan lines are interlaced.

4. An ultrasonic scanning system as in claim 4 including four ultrasonic transducers disposed at 90° with respect to one another whereby each transducer scans one sector and first scan line in four and wherein the beginning of the sectors is controlled so that the scan lines of the transducers are interlaced 1, 3, 2, 4 whereby the time difference between adjacent scan lines is minimized for a four sector interlace.

5. An ultrasonic scanning system as in claim 1 wherein said transducers are angularly disposed on a rotating member whereby as the member is rotated they sequentially scan and predetermined scan sector in a predetermined time and wherein said means for generating a signal corresponding to the beginning of each scan sector includes means for generating the signal responsive to the rotation of the rotating member.

6. An ultrasonic scanning system as in claim 2 wherein said display means comprises a cathode ray tube in which an electron beam impinges upon a display screen and which includes horizontal and vertical deflection means for controlling position of the beam and means for controlling the intensity of the beam, said processed signal serving to cause the beam to scan a sector with a plurality of display lines corresponding to the scan lines and to control the intensity in accordance with the intensity of the recorded signal.

7. An ultrasonic scanning system as in claim 3 wherein said display means comprises a cathode ray tube in which an electron beam impinges upon a display screen and which includes horizontal and vertical deflection means and for controlling the position of the beam and means for controlling the intensity of the beam, said processed signal serving to cause the beam to scan a sector with a plurality of display lines corresponding to the scan lines and to control the intensity in accordance with the intensity of the recorded signal.

8. An ultrasonic scanning system as in claim 4 wherein said display means comprises a cathode ray tube in which an electron beam impinges upon a display screen and which includes horizontal and vertical deflection means for controlling the position of the beam and means for controlling the intensity of the beam, said processed signal serving to cause the beam to scan a sector with a plurality of display lines corresponding to the scan lines and to control the intensity in accordance with the intensity of the recorded signal.

9. An ultrasonic scanning system including at least one ultrasonic transducer adapted to receive electrical pulses and transmit an ultrasonic beam and to receive ultrasonic energy reflected from interfaces and generate an electrical signal corresponding thereto, means for moving said transducer so that its beam periodically scans a predetermined sector in a predetermined time, means for applying pulses to the transducer at a predetermined rate to form a plurality of ultrasonic pulses which travel in scan lines in said sector, the predetermined time and predetermined rate determining the number of scan lines in each sector, a display means of the type in which the display is formed by traces, means for initiating said traces synchronously with the ultrasonic beam scan sector and scan lines so that it forms a sector with a corresponding number of lines, means responsive to said transducer output for modulating the intensity of said trace whereby the intensity of the display represents ultrasonic interfaces in said scanned sector, a video recording means connected to said scanning system and serving to snychronously record a composite signal including information respecting the beginning of each scan sector, scan line and the transducer output whereby when the recording is later reproduced, processed and applied to said display means it forms a display corresponding to the initial display.

10. An ultrasonic scanning system including at least one ultrasonic transducer adapted to receive electrical pulses and transmit an ultrasonic beam and to receive ultrasonic energy and generate an electrical signal, means for moving said transducer so that the beam periodically scans a predetermined sector in a predetermined time, means for applying pulses to the transducer at a predetermined rate to form a plurality of ultrasonic pulses which travel in scan lines, the predetermined time and the pulse rate determining the number of scan lines scanned in each sector, a video recording means connected to said scanning system and serving to synchronously record a signal including information respecting the scan lines, the position of the transducer and the transducer output whereby when the recording is reproduced, processed and applied to control a display means the display means forms a display of the scanned sector.

11. An ultrasonic scanning system as in claim 10 including means for processing the information respecting the position of the transducer and scan line and the transducer output and for directly applying the processed information to a display means during recording whereby said display means forms a display of the information which is being recorded.

12. An ultrasonic scanning system as in claim 10 wherein said display means comprises a cathode ray tube in which an electron beam impinges upon a display screen and which includes horizontal and vertical deflection means for controlling position of the beam and means for controlling the intensity of the beam, said means for receiving the processed reproduced signal and serving to cause the beam to scan a sector with a plurality of display lines corresponding to the scan lines and to control the intensity in accordance with the intensity of the recorded signal.

* * * * *